(12) United States Patent
McFarland et al.

(10) Patent No.: US 6,441,901 B2
(45) Date of Patent: *Aug. 27, 2002

(54) OPTICAL SYSTEMS AND METHODS FOR RAPID SCREENING OF LIBRARIES OF DIFFERENT MATERIALS

(75) Inventors: Eric W. McFarland, San Jose; Earl Danielson, Palo Alto; William Archibald, Hillsborough, all of CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/874,758

(22) Filed: Jun. 5, 2001

Related U.S. Application Data

(60) Division of application No. 09/474,344, filed on Dec. 29, 1999, which is a continuation of application No. 08/947,085, filed on Oct. 8, 1997, now Pat. No. 6,034,775, which is a continuation-in-part of application No. 08/898,715, filed on Jul. 22, 1997, now Pat. No. 6,030,917.
(60) Provisional application No. 60/050,949, filed on Jun. 13, 1997, provisional application No. 60/028,106, filed on Oct. 9, 1996, provisional application No. 60/029,255, filed on Oct. 25, 1996, provisional application No. 60/035,366, filed on Jan. 10, 1997, provisional application No. 60/048,987, filed on Jun. 9, 1997, provisional application No. 60/028, 105, filed on Oct. 9, 1996, and provisional application No. 60/035,202, filed on Jan. 10, 1997.

(51) Int. Cl.[7] .................................................. G01J 4/00

(52) U.S. Cl. ........................ 356/364; 356/369; 356/368

(58) Field of Search ................................. 356/364, 368, 356/369, 370; 324/223, 212, 46

(56) References Cited

U.S. PATENT DOCUMENTS

| 4,455,741 A | 6/1984 | Kolodner |
| 4,563,093 A | 1/1986 | Tada et al. |
| 4,819,658 A | 4/1989 | Kolodner |
| 4,922,200 A | 5/1990 | Jackson et al. |

(List continued on next page.)

OTHER PUBLICATIONS

Chang, H. et al., "Combinatorial Synthesis and High Throughput Evaluation of Ferroelectric/Dielectric Thin–Film Libraries for Microwave Applications".

(List continued on next page.)

Primary Examiner—Frank G. Font
Assistant Examiner—Roy M. Punnoose
(74) Attorney, Agent, or Firm—Dobrusin & Thennisch PC (57) ABSTRACT

Methods and apparatus for screening diverse arrays of materials are provided. In particular, techniques for rapidly characterizing compounds in arrays of materials in order to discover and/or optimize new materials with specific desired properties are provided. The substrate can be screened for materials having useful properties, and/or the resulting materials can be ranked, or otherwise compared, for relative performance with respect to useful properties or other characterizations. In particular, systems and methods are provided for screening a library of magnetic materials for their bulk magnetization, saturation magnetization, and coercivity by imaging their individual optical Kerr rotation, screening a library of dielectric materials for their dielectric coefficients by imaging their individual electro-optical rotation and screening a library of luminescent materials by imaging their individual luminescent properties under a variety of excitation conditions. Optical or visible luminescence systems are also provided as well as their application to screening libraries of different materials.

23 Claims, 8 Drawing Sheets

U.S. PATENT DOCUMENTS

| | | |
|---|---|---|
| 5,124,635 A | 6/1992 | Henley |
| 5,239,365 A | 8/1993 | Inoue |
| 5,311,284 A | 5/1994 | Nishino |
| 5,394,752 A | 3/1995 | Reda |
| 5,446,334 A | 8/1995 | Gaffney |
| 5,450,205 A | 9/1995 | Sawin et al. |
| 5,653,539 A | 8/1997 | Rosengaus |
| 5,776,359 A | 7/1998 | Schultz et al. |
| 5,850,284 A | 12/1998 | Schoeffler et al. |
| 5,959,297 A | 9/1999 | Weinberg et al. |
| 5,985,356 A | 11/1999 | Schultz et al. |
| 6,004,617 A | 12/1999 | Schultz et al. |
| 6,013,199 A | 1/2000 | McFarland |
| 6,030,917 A | 2/2000 | Weinberg et al. |
| 6,034,775 A | 3/2000 | McFarland et al. |
| 6,043,363 A | 3/2000 | LaPointe et al. |
| 6,045,671 A | 4/2000 | Wu et al. |
| 6,087,181 A | 7/2000 | Cong |
| 6,151,123 A | 11/2000 | Nielsen |
| 6,203,726 B1 | 3/2001 | Danielson et al. |

OTHER PUBLICATIONS

Sun, Xiao–Dong et al., "Solution–Phase Synthesis of Luminescent Materials Libraries", Advanced Materials, 1997, pp. 1046–1049.

Takeuchi, I. et al., "Combinatorial Synthesis and Evaluation of Epitaxial Ferroelectric Device Libraries".

OPTICAL SYSTEMS AND METHODS FOR RAPID SCREENING OF LIBRARIES OF DIFFERENT MATERIALS

CROSS REFERENCE TO RELATED APPLICATIONS

This application is a division of Pat. No. 09/474,344, filed Dec. 29, 1999, which is a continuation of Pat. No. 08/947,085, filed Oct. 8, 1999, Pat. No. 6,034,775, which is a continuation-in-part of commonly assigned U.S. patent application Ser. No. 08/898,715, filed Jul. 22, 1997, now U.S. Pat. No. 6,030,917 and a continuation-in-part of commonly assigned, now abandoned U.S. Provisional Applications Ser. Nos. 60/050,949, filed Jun. 13, 1997; 60/028,106, filed Oct. 9, 1996; 60/029,255, filed Oct. 25, 1996; 60/035,366, filed Jan. 10, 1997; 60/048,987, filed Jun. 9, 1997; 60/028,105, filed Oct. 9, 1996; and 60/035,202, filed Jan. 10, 1997; the complete disclosures of which are incorporated herein by reference for all purposes.

This application is also related to commonly assigned, co-pending U.S. patent applications Ser. Nos. 08/327,513, filed Oct. 18, 1994, now U.S. Pat. No. 5,895,356 08/438,043, filed May 8, 1995, now U.S. Pat. No. 5,776,359 and 08/841,423, filed Apr. 22, 1997; now U.S. Pat. No. 6,045,671 commonly assigned U.S. Provisional Application Ser. No. 60/016,102, filed Jul. 23, 1996; and PCT Application No. WO 95/13278, filed Oct. 18, 1995; the complete disclosures of which are incorporated herein by reference for all purposes.

FIELD OF THE INVENTION

The present invention generally relates to methods and apparatus for rapidly screening an array of diverse materials that have been created at known locations on a single substrate surface. More specifically, the invention is directed to optical techniques of screening libraries of different materials.

BACKGROUND OF THE INVENTION

The discovery of new materials with novel chemical and physical properties often leads to the development of new and useful technologies. Currently, there is a tremendous amount of activity in the discovery and optimization of materials, such as superconductors, zeolites, magnetic materials, phosphors, catalysts, thermoelectric materials, high and low dielectric materials and the like. Unfortunately, even though the chemistry of extended solids has been extensively explored, few general principles have emerged that allow one to predict with certainty the composition, structure and reaction pathways for the synthesis of such solid state compounds.

The preparation of new materials with novel chemical and physical properties is at best happenstance with our current level of understanding. Consequently, the discovery of new materials depends largely on the ability to synthesize and analyze new compounds. Given approximately 100 elements in the periodic table that can be used to make compositions consisting of two or more elements, an incredibly large number of possible new compounds remains largely unexplored. As such, there exists a need in the art for a more efficient, economical and systematic approach for the synthesis of novel materials and for the screening of such materials for useful properties.

One of the processes whereby nature produces molecules having novel functions involves the generation of large collections (libraries) of molecules and the systematic screening of those collections for molecules having a desired property. An example of such a process is the humoral immune system which in a matter of weeks sorts through some $10^{12}$ antibody molecules to find one which specifically binds a foreign pathogen (Nisonoff et al., *The Antibody Molecule* (Academic Press, New York, 1975)). This notion of generating and screening large libraries of molecules has recently been applied to the drug discovery process.

Applying this logic, methods have been developed for the synthesis and screening of large libraries (up to $10^{14}$ molecules) of peptides, oligonucleotides and other small molecules. Geysen et al., for example, have developed a method wherein peptide syntheses are carried out in parallel on several rods or pins (*J. Immun. Meth.* 102:259–274 (1987), incorporated herein by reference for all purposes). Generally, the Geysen et al. method involves functionalizing the termini of polymeric rods and sequentially immersing the termini in solutions of individual amino acids. In addition to the Geysen et al. method, techniques have recently been introduced for synthesizing large arrays of different peptides and other polymers on solid surfaces. Pirrung et al. have developed a technique for generating arrays of peptides and other molecules using, for example, light-directed, spatially-addressable synthesis techniques (U.S. Pat. No. 5,143,854 and PCT Publication No. WO 90/15070, incorporated herein by reference for all purposes). In addition, Fodor et al. have developed a method of gathering fluorescence intensity data, various photosensitive protecting groups, masking techniques, and automated techniques for performing light-directed, spatially-addressable synthesis techniques (Fodor et al., PCT Publication No. WO 92/10092, the teachings of which are incorporated herein by reference for all purposes).

Using these various methods, arrays containing thousands or millions of different elements can be formed (U.S. patent application Ser. No. 08/805,727, filed Dec. 6, 1991, now U.S. Pat. No. 5,941,728 the complete disclosure of which is incorporated herein by reference for all purposes). As a result of their relationship to semiconductor fabrication techniques, these methods have come to be referred to as "Very Large Scale Immobilized Polymer Synthesis," or "VLSIPS™" technology. Such techniques have met with substantial success in screening various ligands such as peptides and oligonucleotides to determine their relative binding affinity to a receptor such as an antibody.

The solid phase synthesis techniques currently being used to prepare such libraries involve the sequential coupling of building blocks to form the compounds of interest. For example, in the Pirrung et al. method polypeptide arrays are synthesized on a substrate by attaching photoremovable groups to the surface of the substrate, exposing selected regions of the substrate to light to activate those regions, attaching an amino acid monomer with a photoremovable group to the activated region, and repeating the steps of activation and attachment until polypeptides of the desired length and sequence are synthesized. These solid phase synthesis techniques cannot readily be used to prepare many inorganic and organic compounds.

In PCT WO 96/11878, the complete disclosure of which is incorporated herein by reference, methods and apparatus are disclosed for preparing a substrate with an array of diverse materials deposited in predefined regions. Some of the methods of deposition disclosed in PCT WO 96/11878 include sputtering, ablation, evaporation, and liquid dispensing systems. Using the disclosed methodology, many classes of materials can be generated combinatorially including inorganics, intermetallics, metal alloys, and ceramics.

In general, combinatorial chemistry refers to the approach of creating vast numbers of compounds by reacting a set of starting chemicals in all possible combinations. Since its introduction into the pharmaceutical industry in the late 80's, it has dramatically sped up the drug discovery process and is now becoming a standard practice in the industry (*Chem. Eng. News* Feb. 12, 1996). More recently, combinatorial techniques have been successfully applied to the synthesis of inorganic materials (G. Briceno et al., *SCIENCE* 270, 273–275, 1995 and X.D. xiang et al., *SCIENCE* 268, 1738–1740, 1995). By use of various surface deposition techniques, masking strategies, and processing conditions, it is now possible to generate hundreds to thousands of materials of distinct compositions per square inch. These materials include high $T_c$ superconductors, magnetoresistors, and phosphors. Discovery of heterogeneous catalysts will no doubt be accelerated by the introduction of such combinatorial approaches.

A major difficulty with these processes is the lack of fast and reliable testing methods for rapid screening and optimization of the materials. Recently, a parallel screening method based on reaction heat formation has been reported (F. C. Moates et al., *Ind. Eng. Chem. Res.* 35, 4801–4803, 1996). For oxidation of hydrogen over a metallic surface, it is possible to obtain IR radiation images of an array of catalysts. The hot spots in the image correspond to active catalysts and can be resolved by an infrared camera.

Screening large arrays of materials in combinatorial libraries creates a number of challenges for existing analytical techniques. For example, traditionally, a heterogeneous catalyst is characterized by the use of a micro-reactor that contains a few grams of porous-supported catalysts. Unfortunately, the traditional method cannot be used to screen a catalyst library generated with combinatorial methods. First, a heterogeneous catalyst library synthesized by a combinatorial chemistry method may contain from a few hundred to many thousands of catalysts. It is impractical to synthesize a few grams of each catalyst in a combinatorial format. Second, the response time of micro-reactors is typically on the order of a few minutes. The time it takes to reach equilibrium conditions is even longer. It is difficult to achieve high-throughput screening with such long response times.

Another challenge with screening catalyst arrays is the low concentration of components that may be present in the reactions. For example, oxidation of ethylene to ethylene oxide can be carried out over a silver-based catalyst (S. Rebsdat et al., U.S. Pat. Nos. 4,471,071 and 4,808,738). For a surface-supported catalyst with an area of 1 mm by 1 mm and the same activity as the industrial catalyst, only about 10 parts per billion (ppb) of ethylene are converted into the desired ethylene oxide when the contact time is one second.

Detection of such low component levels in the presence of several atmospheres of reaction mixture is a challenge to analytical methods. Many analytical techniques, including optical methods such as four-wave mixing spectroscopy and cavity ring-down absorption spectroscopy as well as conventional methods such as GC/MS, are excluded because of poor sensitivities, non-universal detectability, and/or slow response. Therefore an apparatus and methodology for screening a substrate having an array of materials that differ slightly in chemical composition, concentration, stoichiometry, and/or thickness is desirable.

SUMMARY OF THE INVENTION

The present invention provides methods and apparatus for interrogating an array of diverse materials located at predefined regions on a single substrate. Typically, each of the individual materials will be screened or interrogated for the same material characteristic. Once screened, the individual materials may be ranked or otherwise compared relative to each other with respect to the material characteristic under investigation.

In one aspect of the invention, systems and methods are provided for rapidly screening dielectric materials in a combinatorial library. This aspect of the invention utilizes the electric field dependence of the light output from a layer of electroluminescent material applied to the surface of the combinatorial library. By applying a slowly increasing voltage to the library while the output from the electroluminescent material is monitored, the dielectric coefficient of the library elements may be directly compared. In an alternate embodiment, ferro-electric materials are applied to the library and the polarization of light reflected from the ferro-electric layer is monitored while varying the applied voltage.

In another aspect of the invention, systems and methods are provided for the optical detection of temperature heterogeneity in a combinatorial library of materials, such as thermoelectric and catalysis materials. In one embodiment, the library is coated with a liquid crystal layer. After applying a voltage across the library elements, the reflectivity/absorption of the liquid crystal layer is monitored with a position sensitive imaging system. The image of the liquid crystal layer reflects any variations in the underlying material's temperature.

In another aspect of the invention, Kerr effect imaging is utilized. A uniform material with a known Kerr is first deposited on the library. The deposited material has a thickness on the order of the extinction length of the optical photon wavelength of the highest Kerr rotation. Thus the Kerr rotation in the deposited layer reflects the magnetization of the underlying library element. By applying an external magnetic field of variable orientation, a traditional B-H curve is generated for each library element from which coercivity may be directly obtained.

In another aspect of the invention, a high throughput screening system is used to characterize the relative radiance, luminance, and chromaticity of materials with respect to excitation energy and spectral output. In one embodiment a library of materials is illuminated with a suitable source. The resulting photon emission from the library materials is filtered with a spectral filter and compared to standards of known radiance, luminance, and chromaticity.

In another aspect of the invention, identification and characterization of gas phase products or volatile components of the condensed phase products is achieved using optical spectroscopy. In these embodiments, library elements are typically activated by a heat source serially or in parallel. A first embodiment employs ultraviolet and visible emission-excitation spectroscopy implemented in a scanning configuration by scanning a laser excitation source over the catalytic surface and monitoring the emission with an energy specific, single photon detector. A second embodiment employs a scanning multi-wave mixing fluorescence imaging system that uses a degenerate four-wave mixing optical technique. This technique relies on the interaction of three coherent light beams to induce a nonlinear polarization in a medium through the third order term of the susceptibility tensor. This induced polarization generates the fourth coherent beam. A third embodiment employs photon scattering analysis to monitor relative and time varying differences in the molecular weight distribution and average molecular weight of a library. In particular, liquid products and reactants of a library of catalysts are monitored by changes in the relative intensity of scattered light measured as a function of the angle relative to the incident beam.

A further understanding of the nature and advantages of the inventions herein may be realized by reference to the remaining portions of the specification and the attached drawings.

DETAILED DESCRIPTION OF THE INVENTION AND PREFERRED EMBODIMENTS

Glossary

The following terms are intended to have the following general meanings as used herein.

Substrate: A substrate is a material having a rigid or semi-rigid surface. In many embodiments at least one surface of the substrate will be substantially flat. In some embodiments the substrate will contain physical separations between synthesis regions for different materials. Suitable physical separations include, for example, dimples, wells, raised regions, and etched trenches. According to other embodiments, small beads or pellets may be provided on the surface, either alone or within substrate surface dimples. The surface area of the substrate is designed to meet the requirements of a particular application. Typically, the surface area of the substrate is in the range of 1 cm$^2$ to 400 cm$^2$. However, other sizes may be used with the present invention, for example surface areas as small as 0.001 cm$^2$ or as large as 10 m$^2$ are possible.

Predefined Region: A predefined region is a localized area on a substrate that is, was, or is intended to be used for the formation of a specific material. The predefined region may be referred to, in the alternative, as a "known" region, a "reaction" region, a "selected" region, or simply a "region." The predefined region may have any convenient shape, e.g., linear, circular, rectangular, elliptical, or wedge-shaped. Additionally, the predefined region can be a bead or pellet which is coated with the component(s) of interest. In this embodiment, the bead or pellet can be identified with a tag, such as an etched binary bar code, that can be used to identify which components were deposited on the bead or pellet. The area of the predefined regions depends on the application and is typically smaller than about 25 cm$^2$. However, the predefined regions may be smaller than 10 cm$^2$, smaller than 5 cm$^2$, smaller than 1 cm$^2$, smaller than 1 mm$^2$, smaller than 0.5 mm$^2$, smaller than 10,000 $\mu$m$^2$, smaller than 1,000 $\mu$m$^2$, smaller than 100 $\mu$m$^2$, or even smaller than 10 $\mu$m$^2$.

Radiation: Radiation refers to energy with a wavelength between $10^{-14}$ and $10^4$. Examples of such radiation include electron beam radiation, gamma radiation, x-ray radiation, ultraviolet radiation, visible light, infrared radiation, microwave radiation, and radio waves. Irradiation refers to the application of radiation to a material or object.

Component: Component is used herein to refer to each of the individual substances that are deposited onto a substrate. Components can act upon one another to produce a particular material. Components can react directly with each other or with an external energy source such as radiation, an electric field, or a magnetic field. A third material or a chemical substance can also act upon components. A component can be an element, a chemical, a material, or a mixture of elements and chemicals. Components can form layers, blends or mixtures, or combinations thereof.

Source Material: The term source material is used herein to refer to the original material from which a component was derived. Source materials can be composed of elements, compounds, chemicals, molecules, etc. that are dissolved in a solvent, vaporized, evaporated, boiled, sublimed, ablated, etc., thus allowing the source materials to deposit onto a substrate during the synthesis process.

Resulting Material: The term resulting material is used herein to refer to the component or combination of components that have been deposited onto a predefined region of a substrate. The resulting materials may comprise a single component, or a combination of components that have reacted directly with each other or with an external source. Alternatively, the resulting material may comprise a layer, blend or mixture of components on a predefined region of the substrate. The resulting materials are screened for specific properties or characteristics to determine their relative performance.

Mixture or Blend: The term mixture or, interchangeably, blend refers to a collection of molecules, ions, electrons, or chemical substances. Each component in the mixture can be independently varied. A mixture can consist of two or more substances intermingled with no constant percentage composition, wherein each component may or may not retain its essential original properties, and where molecular phase mixing may or may not occur. In mixtures, the components making up the mixture may or may not remain distinguishable from each other by virtue of their chemical structure.

Layer: The term layer is used herein to refer to a material that separates one material, component, substrate or environment from another. A layer is often thin in relation to its area and covers the material beneath it. A layer may or may not be thin or flat, but once it is deposited it generally covers the entire surface such that it separates the component or substrate below the layer from the component or environment above the layer.

Heterogeneous catalysts: Heterogeneous catalysts enable catalytic reactions to occur with the reactants and catalysts residing in different phases. As used herein, heterogeneous catalysts include, but are not limited to, mixed metal oxides, mixed metal nitrides, mixed metal sulfides, mixed metal carbides, mixed metal fluorides, mixed metal silicates, mixed metal aluminates, mixed metal phosphates, nobel metals, zeolites, metal alloys, intermetallic compounds, inorganic mixtures, inorganic compounds, and inorganic salts.

Homogeneous catalysts: Homogeneous catalysts enable catalytic reactions to occur with the reactants and catalysts residing in the same phase. As used herein, homogeneous catalysts include, but are not limited to, catalysts for the polymerization of one or more olefinic or vinyl monomers. The olefinic monomers include, but are not limited to, ethylene or alpha-olefins containing from 3 to 10 carbon atoms, such as propylene, 1-butene, 1-pentene, 1-hexene, and 1-octene. The vinyl monomers include, but are not limited to, vinyl chloride, vinyl acetate, vinyl acrylate, methylmethacrylate, methyl vinyl ether, ethyl vinyl ether and acetonitrile. The catalysts employed to carry out a polymerization of one or more monomers of this type include, but are not limited to, radical catalysts, cationic catalysts, anionic catalysts, and anionic coordination catalysts.

Generating Arrays of Materials

Generally, an array of materials is prepared by successively delivering components of the materials to predefined regions on a substrate, and simultaneously reacting the components to form at least two materials or, alternatively, the components are allowed to interact to form at least two materials. In one embodiment, for example, a first component of a first material is delivered to a first predefined location on a substrate, and a first component of a second material is delivered to a second predefined region on the same substrate. Simultaneously with or thereafter, a second component of the first material is delivered to the first region on the substrate, and a second component of the second material is delivered to the second region on the substrate. Each component can be delivered in either a uniform or gradient fashion to produce either a single stoichiometry or, alternatively, a large number of stoichiometries within a single predefined region. Moreover, the components can be delivered as amorphous films, epitaxial films or lattice or superlattice structures. The process is repeated, with additional components, to form a vast array of components at predefined locations on the substrate. Thereafter, the components are simultaneously reacted to form at least two materials or, alternatively, the components interact to form at least two materials. As described herein, the components can be sequentially or simultaneously delivered to the predefined regions on the substrate using any of a number of different delivery techniques.

Numerous combinatorial techniques can be used to synthesize the various arrays of diverse materials on the substrate according to the present invention. For example, in one embodiment a first component of a first and second material is delivered to the predefined regions on the substrate. Then a second component of the first and second materials is delivered to the predefined regions on the substrate. This process continues for the other components (e.g., third, fourth, fifth, etc. components) and/or the other materials (e.g., third, fourth, fifth, etc. materials) until the array is complete. In another embodiment, the array is formed as previously described, but the resulting materials are formed immediately as the components contact each other on the substrate. In yet another embodiment, the array is formed as previously described, but after the various components are delivered to the substrate, a processing step is carried out which allows or causes the components to interact to form layers, blends, mixtures, and/or materials resulting from a reaction between components. In still another embodiment, two or more components are delivered to the predefined regions on the substrate using fast sequential or parallel delivery techniques such that the components interact with each other before contacting the substrate. The resulting array of materials, each at a discrete and known location on the substrate, comprises layers, blends, mixtures, and/or materials resulting from a reaction between components.

Essentially, any conceivable substrate can be employed in the invention. The substrate can be organic, inorganic, biological, nonbiological, or a combination thereof. The substrate can exist as particles, strands, precipitates, gels, sheets, tubing, spheres, containers, capillaries, pads, slices, films, plates, slides, etc. The substrate can have any convenient shape, such as a disc, square, sphere, circle, etc. The substrate is preferably flat, but may take on a variety of alternative surface configurations. For example, the substrate may contain raised or depressed regions on which the synthesis of diverse materials takes place. The substrate and its surface preferably form a rigid support on which to carry out the reactions described herein. The substrate may be any of a wide variety of materials including, for example, polymers, plastics, pyrex, quartz, resins, silicon, silica or silica-based materials, carbon, metals, inorganic glasses, inorganic crystals, and membranes Upon review of this disclosure, other substrate materials will be readily apparent to those of skill in the art. Surfaces on the solid substrate can be composed of the same materials as the substrate or, alternatively, they can be different (ie., the substrates can be coated with a different material). Moreover, the substrate surface can contain thereon an adsorbent (for example, cellulose) to which the components of interest are delivered. The most appropriate substrate and substrate-surface materials will depend on the class of materials to be synthesized and the selection in any given case will be readily apparent to those of skill in the art. In other embodiments, the substrate can be a series of small beads or pellets. As with the single substrate having an array of materials thereon, each of the individual beads or pellets can be screened for materials having useful properties.

A variety of substrate systems are possible, including two- and three-dimensional substrate systems. In some embodiments, the two-dimensional combinatorial catalysis library will be deposited either on a porous substrate, such as alumina, or on a non-porous substrate. In some embodiments, the substrate will further contain a synthesis support. The synthesis support can be made of alumina, silicon, quartz, zeolites, Teflon, silica and other oxides, etc.

The synthesis support may be in the form of beads, discs or any other geometry in, for example, one of the following substrate configurations: i) a porous support placed in wells wherein the reactants flow through the support from the top of the wells out through a hole in the bottom of the wells (or flow may be in the reverse direction); ii) a porous support placed in wells wherein the reactants do not flow through from the top to the bottom of the wells, but only to and from the top of the wells; iii) a non-porous support placed in wells wherein the reactants flow around the support from the top of the wells out through a hole in the bottom of the wells (or flow may be in the reverse direction); iv) a non-porous support placed in wells wherein the reactants do not flow through from the top to the bottom of the wells, but only to and from the top of the wells; or v) a porous or non-porous support not contained in wells wherein the reactants are deposited directly onto the substrate surface.

Figure 1:
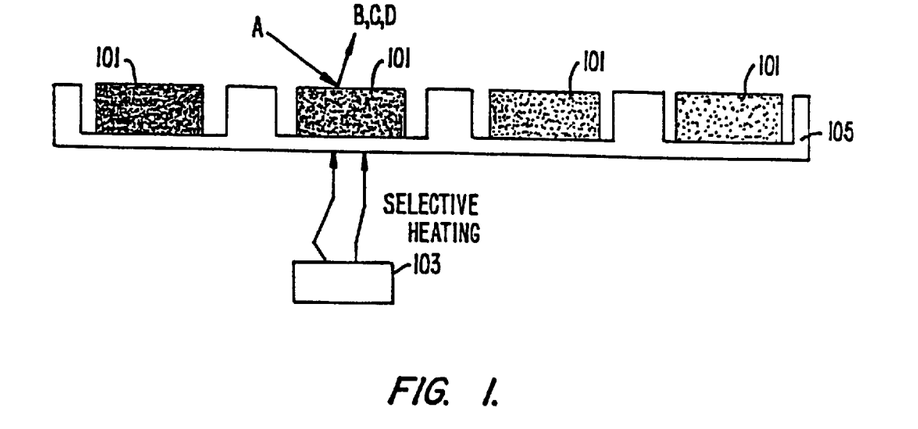
FIG. 1 illustrates a configuration for selective heating of materials on a substrate according to the present invention.

For instance, in one possible configuration illustrated in FIG. 1, a sample chamber (not shown) is filled with reactant gas A at a pressure P. Focused IR heating from source 103 selectively activates individual catalyst elements 101 contained on an array substrate 105. Alternatively, resistive heating elements (not shown) can be incorporated into substrate 105. All of the library elements 101 are in contact with reactant gas A; however, only when heated will the catalyst posses significant activity to produce appreciable products. If necessary the library can be cooled to avoid any side reactions.

Figure 2:
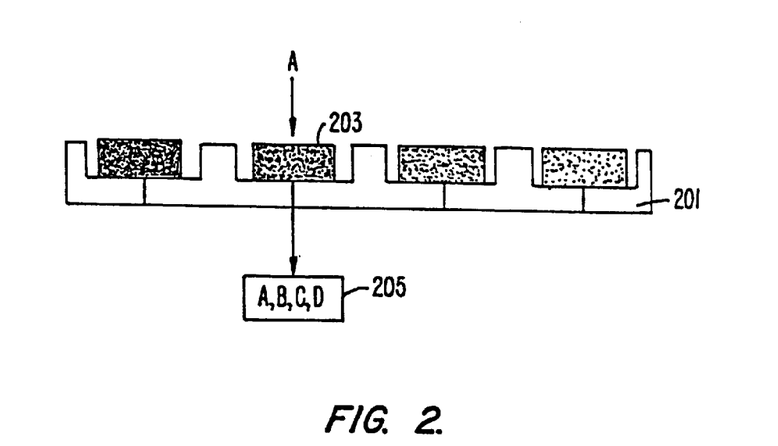
FIG. 2 illustrates a permeable substrate according to the invention, wherein a reactant gas is driven through a supported library.

In a second possible configuration illustrated in FIG. 2, a permeable substrate 201 is utilized. Thus reactant gas A at a pressure P on top of the library is driven through the supported catalyst library element 203 and then both unreacted reactants and products pass through the porous substrate into a region of lower pressure 205 where the products are detected. The flow can be directed though one element path at a time by sealed conduits or, alternatively, it can be directed through all elements simultaneously. Individual elements can be selectively heated for serial measurement of the products or the entire library heated for parallel characterization (e.g., optical emission imaging). This method has the advantage that the pressure drop across the substrate allows the gas detection system to sample a lower pressure stream. In the case of liquid or solid phase products, volatile components of the products can be sampled identically to the gas phase products. For products with insufficient vapor pressure, scanned infrared laser heating or individual resistive element heating configurations can be used.

Generally, physical masking systems can be employed in combination with various deposition techniques in order to apply components onto a substrate in a combinatorial fashion, thereby creating arrays of resulting materials at predefined locations on the substrate. The arrays of resulting materials will usually differ in composition, stoichiometry and/or thickness across the substrate. The components can, for example, be dispensed to the substrate in the form of a gas, a liquid or a powder. Suitable deposition techniques include, but are not limited to, sputtering, electron-beam and thermal evaporation, laser deposition, ion beam deposition, chemical vapor deposition, and spray-coating. In solution phase deposition techniques include, for example, sol/gel methods, discrete liquid dispensing techniques (e.g. pipettes, syringes, ink jets, etc.), spin coating with lithography, microcontact printing, spraying with masks and immersion impregnation. Moreover, such dispenser systems can be manual or, alternatively, they can be automated using, for example, robotics techniques. A more complete description of representative arrays of materials and systems and methods for generating such arrays of materials can be found in commonly assigned, co-pending patent applications "The Combinatorial Synthesis Of Novel Materials", Publication No. WO 95/13278, filed Oct. 18, 1995; "Systems and Methods for the Combinatorial Synthesis of Novel Materials," patent application Ser. No. 08/841,423, filed Apr. 22, 1997; and "Discovery of Phosphor Materials Using Combinatorial Synthesis Techniques," provisional patent application Ser. No. 60/039,882, filed Mar. 4, 1997; the complete disclosures of which are incorporated herein by reference for all purposes.

In some embodiments of the present invention, after the components have been deposited onto predefined regions on a substrate, they are reacted using a number of different techniques. For example, the components can be reacted using solution based synthesis techniques, photochemical techniques, polymerization techniques, template directed synthesis techniques, epitaxial growth techniques, by the sol-gel process, by thermal, infrared or microwave heating, by calcination, sintering or annealing, by hydrothermal methods, by flux methods, by crystallization through vaporization of solvent, etc. Furthermore, each predefined region on the substrate can be heated simultaneously or sequentially using heat sources such as focussed infrared radiation, resistive heating, etc. Reactants can, for example, be dispensed to the library of elements in the form of a gas or a liquid. Other useful techniques that can be used to react the components of interest will be readily apparent to those of skill in the art. Additionally, components can react with each other instantly, upon contacting each other, or in the air before contacting the substrate. The components can also form layers, blends or mixtures, in the air or on the substrate, rather than reacting with each other.

Once prepared, the array of resulting materials can be screened for useful properties using the methods described herein. Either the entire array or, alternatively, a section thereof (e.g., a row of predefined regions) can be screened using parallel or fast sequential screening. In some embodiments, a predefined region on the substrate and, therefore, the area upon which each distinct material is synthesized, is smaller than about 25 cm$^2$, less than 10 cm$^2$, less than 5 cm$^2$, less than 1 cm$^2$, less than 1 mm$^2$, or less then 0.5 mm$^2$. In other embodiments, the regions have an area less than about 10,000 $\mu$m$^2$, less than 1,000 $\mu$m$^2$, less than 100 $\mu$m$^2$, or less than 10 $\mu$m$^2$. Accordingly, the density of regions per unit area will be greater than 0.04 regions/cm$^2$, greater than 0.1 regions/cm$^2$, greater than 1 region/cm$^2$, greater than 10 regions/cm$^2$, or greater than 100 regions/cm$^2$. In other embodiments, the density of regions per unit area will be greater than 1,000 regions/cm$^2$, greater than 10,000 regions/cm$^2$, greater than 100,000 regions/cm$^2$, or greater than 10,000,000 regions/cm$^2$.

In some embodiments, the screening systems of the present invention will be used to screen a single substrate having at least 9 different materials. In other embodiments, the screening system scans a single substrate having more than 50, 100, 10$^3$, 10$^4$, 10$^5$, 10$^6$, or more materials synthesized thereon. In some embodiments, the substrate will comprise arrays of materials with as few as two components, although the substrate can have materials with 3, 4, 5, 6, 7, 8 or more components therein. The substrate can be screened for materials having useful properties and/or the resulting materials can be ranked, or otherwise compared, for relative performance with respect to useful properties or other characteristics. Resulting materials include, but are not limited to, covalent network solids, ionic solids and molecular, inorganic materials, intermetallic materials, metal alloys, ceramic materials, organic materials, organometallic materials, non-biological organic polymers, composite materials (e.g., inorganic composites, organic composites, or combinations thereof), or homogeneous or heterogeneous catalysts. Again, once useful resulting materials have been identified using the methods of the present invention, a variety of different methods can be used to prepare such materials on a large or bulk scale with essentially the same structure and properties. Properties which can be screened for include, but are not limited to, electrical, thermal, mechanical, morphological, optical, magnetic, chemical, conductivity, super-conductivity, resistivity, thermal conductivity, anisotropy, hardness, crystallinity, optical transparency, magnetoresistance, permeability, frequency doubling, photoemission, coercivity, dielectric strength, or other useful properties which will be apparent to those of skill in the art upon review of this disclosure. Importantly, the synthesizing and screening of a diverse array of resulting materials enables new compositions with new physical properties to be identified.

Given the chemical complexity of catalytic systems, the lack of predictive models, the number of possible combinations of metals, counterions, ligands, and supports, and the time consuming process of evaluating the performance of each catalyst formulation utilizing conventional laboratory pilot reactors, it is not surprising that the search for the optimum catalyst is a time consuming and inefficient process. Thus, a combinatorial approach to the discovery and optimization of catalytic systems, which combines the synthesis of catalyst libraries with the screening tools of this invention, is useful for accelerating the pace of research in this field. The catalyst libraries of the present invention can include organic (e.g., catalytic antibodies), organometallic, heterogeneous or solid state inorganic array elements. Organometallic catalyst libraries which can be screened for useful catalytic properties include, but are not limited to, those described in co-pending U.S. patent application Ser. No. 08/898,715, filed Jul. 22, 1997, which is hereby incorporated by reference for all purposes.

Catalyst libraries comprising inorganic (e.g., heterogeneous and solid state inorganic) materials can also be screened for useful properties using the methods of this invention. Catalyst libraries can comprise powders, impregnated solid supports, inorganic films and monoliths, or crystals that are spatially separated within a substrate system (e.g., wells, fiat surfaces). Solid state inorganic materials useful as heterogeneous catalysts are well known in the chemical industry. Heterogeneous catalysts enable catalytic reactions to occur with the reactants and catalysts residing in different phases and include, but are not limited to, mixed metal oxides, mixed metal nitrides, mixed metal sulfides, mixed metal carbides, mixed metal fluorides, mixed metal silicates, mixed metal aluminates, mixed metal phosphates, nobel metals, zeolites, metal alloys, intermetallic compounds, inorganic mixtures, inorganic compounds, and inorganic salts. Heterogeneous catalyst systems typically comprise metals, metal oxides, metal sulfides, and other metal salts, can be supported on a carrier (e.g., alumina, silica of controlled particle size and porosity), and can be used in bulk.

Heterogeneous catalysts can be prepared by a number of methods which are well known in the art and include mixing reactive solutions, impregnation of solutions of metal salt precursors onto or into solid carriers, coprecipitation, and mixing colloidal dispersions. These methods yield chemically complex, multicomponent solid products that can be further treated with reducing agents, oxidizing agents and other third components and modifiers to produce optimized materials.

Once an array of catalysts is formed, the screening methods of the present invention can be used to characterize the catalytic properties of the various compounds by observing, for example, activity, lifetime and selectivity for a variety of catalytic transformations. For purposes of this invention, a catalyst is defined as any material that accelerates the rate of a chemical reaction and which is either not consumed during the reaction or which is consumed at a rate slower (on a molar basis) than the reaction that is being catalyzed. Examples of catalytic reactions/transformations include, but are not limited to, total oxidations (e.g., the conversion of CO into $CO_2$ using oxygen, or $NO_x$ for simultaneous reduction of the $NO_x$), selective oxidations (e.g., epoxidations of olefins), reductions (e.g., hyrdogenation of unsaturated species), polymerizations (e.g., ethylene copolymerizations), dimerization (e.g., ethylene to butene), trimerization, oligomerization, decompositions (e.g., conversion of $NO_x$ into $N_2$ and $O_2$), hydrosilation, carbonylations, hydrocynation, hydroformylation, isomerization, metathesis (e.g., of olefins and acetylenes), carbon-hydrogen activation, cross coupling, Friedel-Crafts acylation and alkylation, hydration, and Diels-Alder reactions.

Optical Spectroscopy Systems for Gas Phase Measurements

The spectroscopic techniques of degenerate four-wave mixing (DFWM) and laser-induced fluorescence (LIF) can be applied to the detection of minor species for combustion diagnostics at high sensitivities (Mann et al., "Detection and Imaging of Nitrogen Dioxide with the Degenerate Four-Wave-Mixing and Laser-Induced-Fluorescence Techniques," =i Applied Optics,Jan. 20, 1996, 35(3) :475–81). In degenerate four-wave mixing the signal is detected as a spatially and temporally coherent beam that relies on a resonant interaction of the light frequency with a molecular transition. Four-wave mixing relies on the interaction of three coherent light beams to induce a nonlinear polarization in a medium through the third order term of the susceptibility tensor. This induced polarization generates the fourth coherent beam. As a result, extreme sensitivity of detection is possible. Due to this enhanced sensitivity, degenerate four-wave mixing may be employed to observe trace quantities of products or reactants in a reactor containing a combinatorial library of active sites. Instantaneous and spatially resolved measurements of both temperature and species' concentration in a flow reactor can be obtained.

Optical Characterization of Condensed Phase Products

Photon Scattering Systems

In yet another aspect of the invention, systems and methods are provided for identifying and characterizing condensed phase products based on the optical properties of the materials in a combinatorial library or array. In a first embodiment, photon scattering analysis is employed to monitor relative and time varying differences in the molecular weight distribution and average molecular weight of the elements of the library. For example, liquid products and reactants of a library of catalysts can be monitored by changes in the relative intensity of scattered light measured as a function of angle relative to an incident beam.

In one embodiment of the invention, a photodiode array is positioned around a library element, the library element being irradiated with a light source such as a laser. This detector array is used to collect the intensity of the scattered light as a function of angle. The array of library elements is scanned relative to the laser-detector assembly for the purpose of mapping the property as a function of position on the library. Several sweeps of the library can be used to characterize the temporal changes in the scattered light distribution, for example to monitor the rate of polymerization.

Although precise quantitative determination of the Rayleigh ratio and average molecular weight requires careful design of the scattering cell geometry (typically cylindrical), for relative measurements, more convenient practical considerations can be used. Similarly, precise work using only small angle scattering allows simplification of the scattering-function and use of the straight-forward Debye equation to determine average molecular weights accurately.

Polarized Light Imaging

Figure 3:
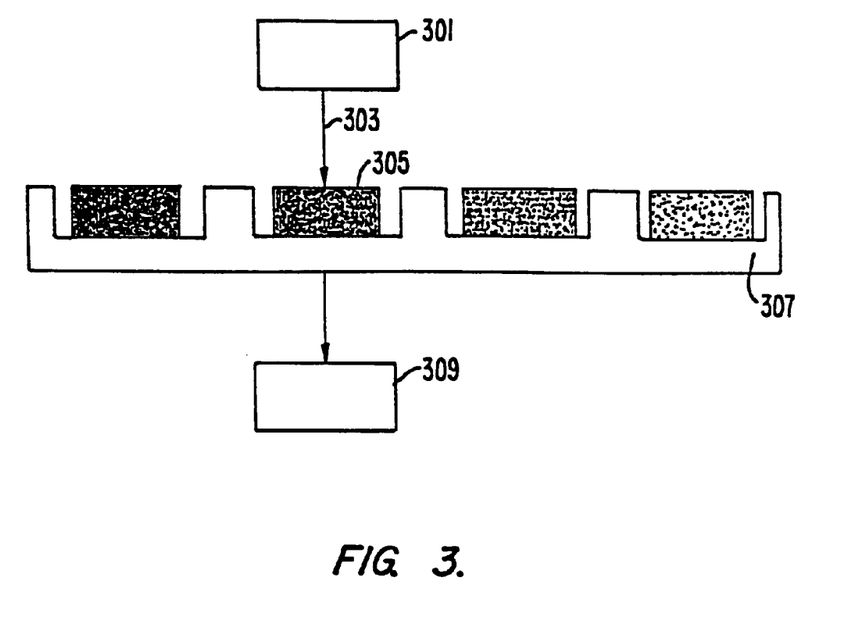
FIG. 3 illustrates a polarized light imaging system according to the invention.

In another embodiment, polarized light imaging systems and methods are provided for characterizing libraries of materials, such as polymers. The formation of optically active crystalline domains in solids can give rise to optical rotation and/or preferential transmission of polarized light. As illustrated in FIG. 3, a polarized light source 301 directs a beam of polarized light 303 towards a library element 305 contained on a transparent array substrate 307. A polarized light detector 309 monitors the transmitted light. Alternatively, the entire library can be simultaneously illuminated with a large diameter beam of polarized light. In this embodiment detector 309 is a CCD array and a polarizer (not shown) is interposed between array 307 and detector 309. This embodiment allows characterization of the relative changes in orientational order to be monitored in real time. Thus activity, for example, the rate of polymerization in a polymer system, can be monitored.

Dielectric Optical Screening

In another aspect of the invention, systems and methods are provided for rapidly screening dielectric materials in a combinatorial library. Specifically, one embodiment of the invention takes advantage of the electric field dependence of the light output from electroluminescent materials.

Figure 4:
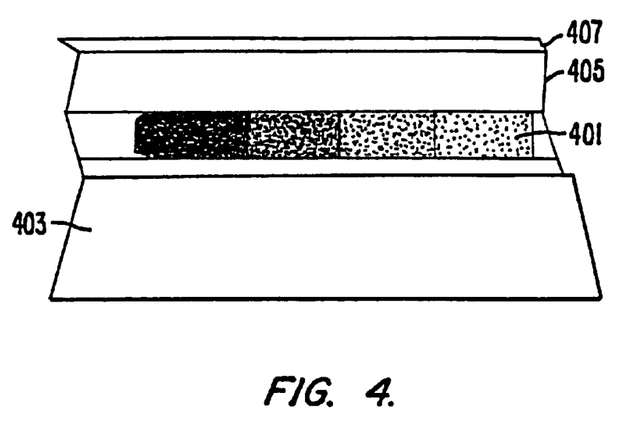
FIG. 4 illustrates an embodiment of the invention used to screen an array of dielectric materials.

FIG. 4 illustrates a combinatorial library 401 synthesized on a conducting substrate 403. If necessary, a conducting coating may be applied to substrate 403. The library of potential dielectric materials is deposited at a uniform thickness of approximately 800 nm to 1200 nm, preferably about 1000 nm. After processing the dielectric library 401, an optically active layer 405 comprising an electroluminescent material (EL), such as ZnS:Mn, or a ferro-electric material is deposited to a uniform thickness of approximately 100–500 nm over library 401. Optically active layer 405 is then covered with a transparent conducting overlayer 407.

Figure 5:
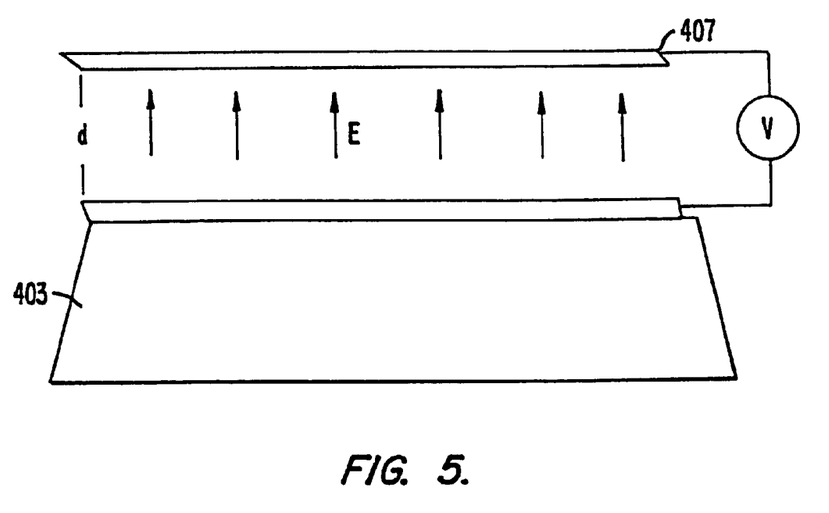
FIG. 5 illustrates the uniform electric field generated in the embodiment shown in FIG. 4.

To monitor the dielectric coefficient of the library elements, a voltage (dc or ac) is applied to conducting layers 403 and 407 and gradually increased until luminescence is observed or until an electro-optic Kerr rotation is observed (see FIG. 5). The electric field in the optically active film 405 directly adjacent to a given library element will depend upon the dielectric coefficient of the library material. The larger the dielectric coefficient of the library element, the higher the electric field in the optically active layer 405 for the same voltage. Thus, the EL layer 405 will luminesce (or the first measurable rotation will occur) at the lowest voltages directly above library elements with the highest dielectric coefficient, E.

Figure 6:
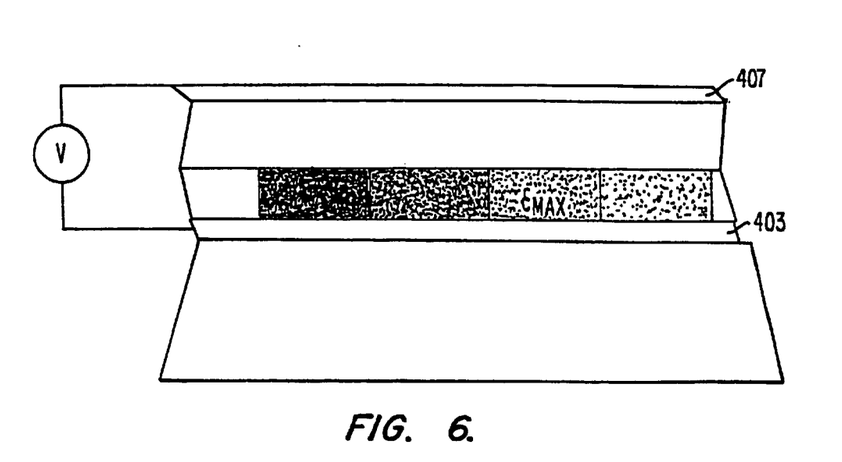
FIG. 6 illustrates an embodiment of the invention used to screen an array of dielectric materials utilizing a ferroelectric material.
Figure 7:
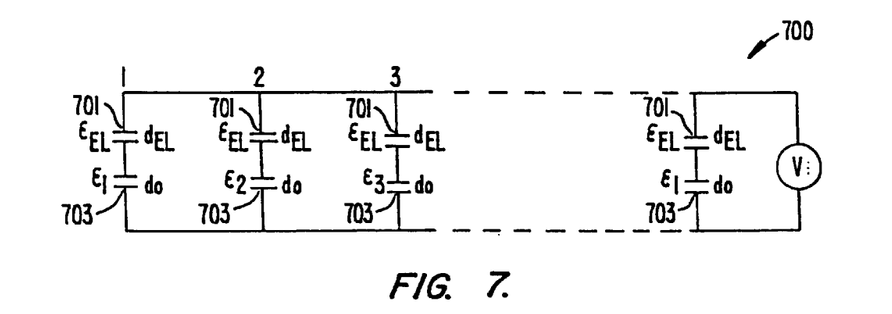
FIG. 7 illustrates a simple model of the embodiment shown in FIG. 6.

As illustrated in FIG. 5, a uniform electric field, E, is produced in the gap between the top and bottom conducting layers such that E equals the applied voltage, V, divided by the separation distance, d. If an EL material of dielectric constant $\in_{EL}$ is placed in the gap, the material sees a uniform field and thus should have a nearly uniform luminous output. Similarly, if a ferro-electric material is placed in the gap and illuminated with polarized light, a rotation of the optical polarization will occur uniformly over the surface. If, however, the library of dielectrics is now inserted into this gap, the spatially varying $\in(r)$ of the library will alter the electric field in the optically active layer 405 and thus alter locally the light output (EL) or polarization change (FE), as illustrated in FIG. 6. A simple model of the library is shown in FIG. 7. In the model, a parallel array 700 of two series capacitors includes a capacitor 701 representing the active layer (e.g., EL) with its dielectric coefficient $\in_{EL}$. A second capacitor, 703, is the dielectric library element with a spatially varying dielectric coefficient $\in_j(r)$.

Assuming a uniform area, $A_o$, above each library element, and assuming that the thickness of the dielectric material, $d_o$, and the active layer, $d_{EL}$, are uniform, the charge, Q, is given by:

$$Q_i = \hat{C}_j V$$

where:

$$\hat{C}_i = \frac{1}{\frac{1}{C_{EL}} + \frac{1}{C_j}}$$

therefore:

$$Q_i = \frac{V}{\frac{1}{C_{EL}} + \frac{1}{C_i}} = \frac{V}{\frac{d_{EL}}{\varepsilon_{EL} A_o} + \frac{d_o}{\varepsilon_j A_o}}$$

The uniform flux density, D, in the two series capacitors is given by:

$$D = \frac{Q_i}{A_o}$$

However, the field between the two capacitors varies as D/∈. Therefore the E field in the EL layer is:

$$E_{EL} = \frac{D_i}{\varepsilon_{EL}} = \frac{V/A_o \varepsilon_{EL}}{\frac{d_{EL}}{\varepsilon_{EL} A_o} + \frac{d_o}{\varepsilon_j A_o}} = \frac{V \varepsilon_j}{d_{EL} \varepsilon_j + d_o \varepsilon_{EL}}$$

Examining the two limits of the library thickness:

For $d_o \times \in_{EL} >> d_{EL} \times \in_j$ $$E_{EL} \approx \frac{V \varepsilon_j}{d_o \varepsilon_{EL}}$$

For $d_o \times \in_{EL} << d_{EL} \times \in_j$ $$E_{EL} \approx \frac{V \varepsilon_j}{d_{EL}}$$

Thus when the library thickness is very large compared with the EL layer the electric field, E, across the EL layer depends linearly on the dielectric coefficient of the library material.

Figure 8:
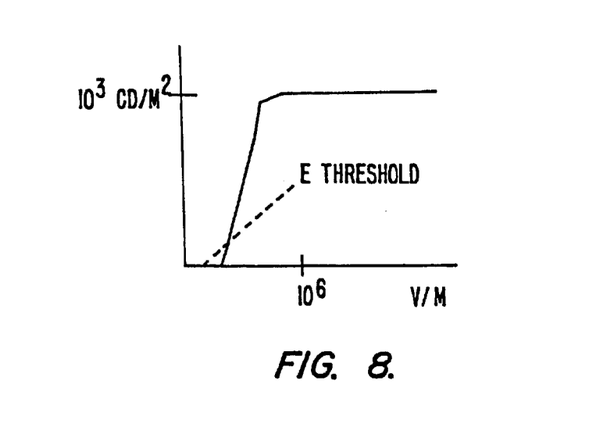
FIG. 8 is a graph of luminance output versus electric field for a typical electroluminescent material.

The measurement is performed by slowly increasing |V|. The first regions where light is detected will have the highest ∈$_j$. Quantification is possible by comparison to a standard dielectric material. However for screening purposes this is not necessary. The particular sensitivity of the method is aided by the typical (log) luminance output versus electric field for a typical EL material, e.g., ZnS:Mn, as illustrated in FIG. 8.

At an approximately $10^6$ volts/m EL threshold for a typically 1000 nm library/EL composite thickness, voltages across the composite will be rather small, typically <10–20V. Similar behavior is observed for ferro-electric materials.

Optical Detection of Temperature Heterogeneity

Figure 9:
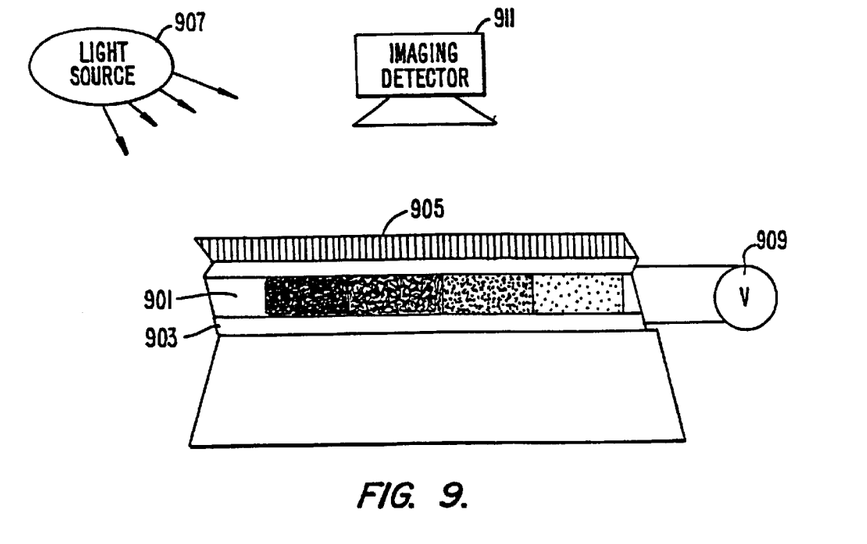
FIG. 9 illustrates an embodiment of the invention used for the optical detection of temperature heterogeneity in a combinatorial array of materials.

In another aspect of the invention, systems and methods are provided for the optical detection of temperature heterogeneity in combinatorial libraries of materials, such as thermoelectric and catalysis materials. In one embodiment of the invention, the temperature sensitive index of refraction of various liquid crystals is utilized. As illustrated in FIG. 9, the thin film library elements 901 are deposited on a low thermal mass substrate 903. Substrate 903 may or may not have additional electrical contacts. After processing the library, the substrate is coated with a liquid crystal layer 905. The system is maintained near the liquid crystal phase transition temperature and illuminated with an appropriate wavelength source lamp 907. The device is then activated by applying a voltage, 909, across the elements. The reflectivity/absorption of the liquid crystal layer 905 is then monitored with an image detector 911, such as a CCD or other two dimensional optical imaging system. The low cost and simplicity of this system has clear advantages for high throughput screening applications.

In this system, materials with substantially identical electrical conductivities are preferably screened since the thermal power through each library element is proportional to the current through that element. With the flow of current, a temperature gradient will be produced across the layer that is dependent upon the Seebeck coefficient of the element. Therefore the higher the Seebeck coefficient, the higher the gradient. The adjacent liquid crystal layer will undergo a phase transition that will alter its absorption/reflection coefficient for the incident light detected by sensor 911. The image of the liquid crystal layer will thus reflect the underlying material's temperature variation.

Figure 10:
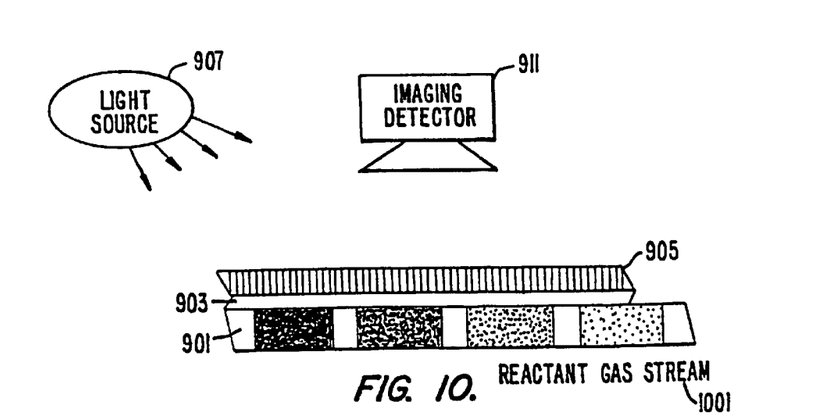
FIG. 10 is an illustration of an alternate configuration of the embodiment shown in FIG. 9 for screening catalysts.

As shown in FIG. 10, similar configurations can be implemented for the screening of catalysts. In these embodiments, substrate 903 is coated with a liquid crystal layer 905 and a reactant gas stream 1001 is applied to the lower surface of substrate 903. The system is maintained near the liquid crystal phase transition temperature and illuminated with an appropriate wavelength source lamp 907. The device is then activated and the reflectivity/absorption of the liquid crystal layer is monitored with image detector 911.

Kerr Imaging of Non-homogenous Magnetic Material

One of the problems existing techniques have encountered in using Kerr microscopy to measure magnetization on heterogeneous two-dimensional surfaces is the variable Kerr coefficient for different materials. Although Kerr microscopy is routinely used to examine materials of homogeneous compositions, it generally cannot be used to compare magnetization in two regions of different materials. The theory of these differences is poorly understood and very little data exists for materials other than the traditional ferromagnetic materials. The invention described herein eliminates the variability of the heterogeneous materials by the addition of a homogenous overlayer such that the Kerr rotation from the overlayer reflects only the underlayer magnetization.

Kerr effect imaging relies on the rotation of light polarization reflected or transmitted from a surface, where the degree of rotation depends upon the surface material's magnetization, M. (i.e., $\Delta\theta=\theta_{in}-\theta_{out}=\theta_{Kerr}\approx\kappa M$). Both longitudinal and polar Kerr effects may be measured depending upon the relative orientation of M and κ. For a combinatorial library of many different materials, κ can vary significantly which makes it extremely difficult to compare M values between different materials.

Figure 11:
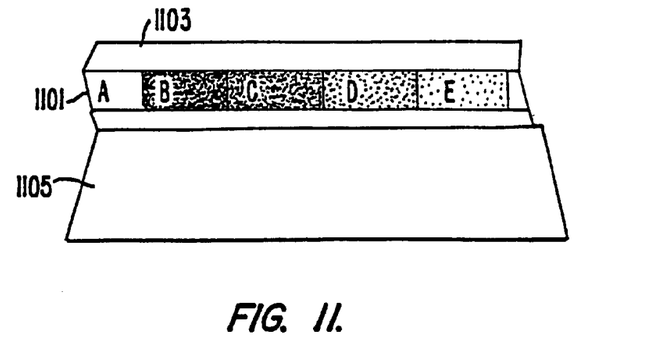
FIG. 11 illustrates an embodiment of the invention used to measure the magnetization of a heterogeneous array of materials.

To overcome this problem, the present invention provides a method comprising the steps of synthesizing and processing a magnetic thin film library 1101 (see FIG. 11). A uniform material 1103 with a known Kerr is deposited on library 1101 at a thickness on the order of the extinction length of the optical photon wavelength of the highest Kerr rotation, e.g., a super parametric material. Optionally, a buffer layer 1105 may be applied to the lower surface of the thin film library 1101. The Kerr rotation in the overlayer 1103 will reflect the magnetization of the underlying library element 1101. Accordingly, the spatially varying $\theta_{Kerr}(r)$ is used to image the underlying magnetic library M(r). By applying an external magnetic field of variable orientation, the orientation of M(r,H) is followed and a traditional B-H curve is then generated for each library element. From the B-H curve, the coercivity and remenance is obtained directly.

Figure 12:
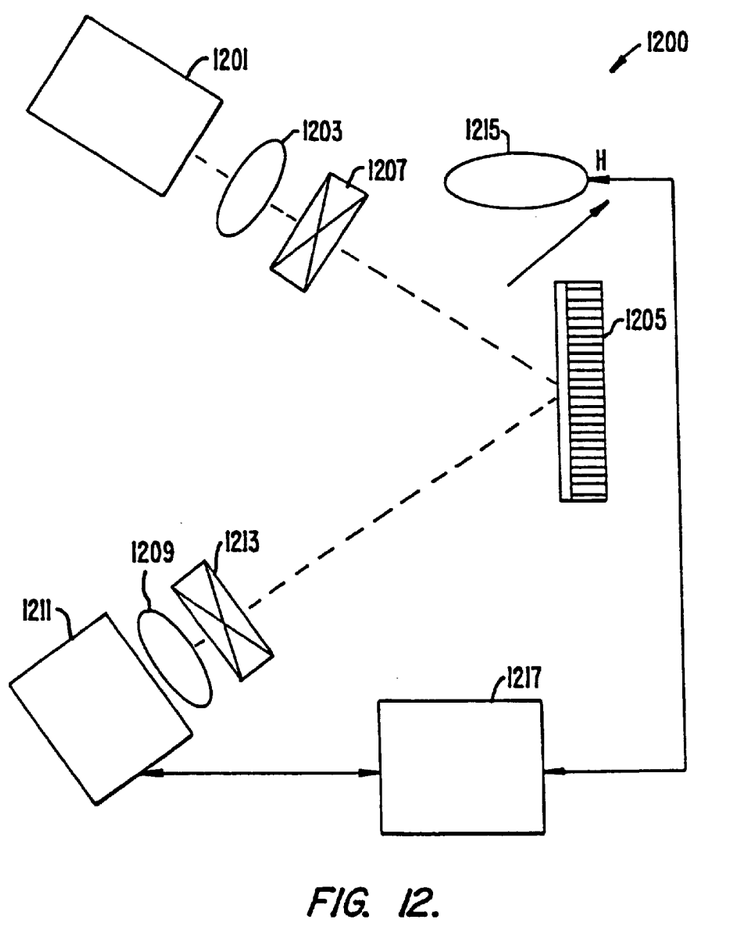
FIG. 12 illustrates a system for measuring the Kerr rotation of different materials of a library of materials.

FIG. 12 illustrates a system 1200 for measuring the Kerr rotation of different materials on a library of materials. Optical system 1200 comprises an incoherent, polarized light source 1201 and an optical train 1203 for projecting the light from source 1201 onto the library 1205 at a near normal incidence angle. Optical train 1203 includes lenses and one or more filters, the filters primarily passing light towards the violet range, thereby optimizing the sensitivity. The optical system also includes a polarizer 1207. The reflected light is passed through collection optics 1209, optics 1209 including appropriate lenses and filters for imaging the reflected light onto a CCD camera 1211 or other position sensitive optical detector. Also included within the optical train is a second polarizer 1213 set near the extinction for the incident beam. A controller 1215 applies a magnetic field H to library 1205. The intensity of the light at each detector pixel is proportional to the Kerr rotation (and thus M) at the corresponding point on the sample. A computer 1217 determines the B-H curve by varying the direction of the applied field H and determining the M for each direction of the field.

Figure 13:
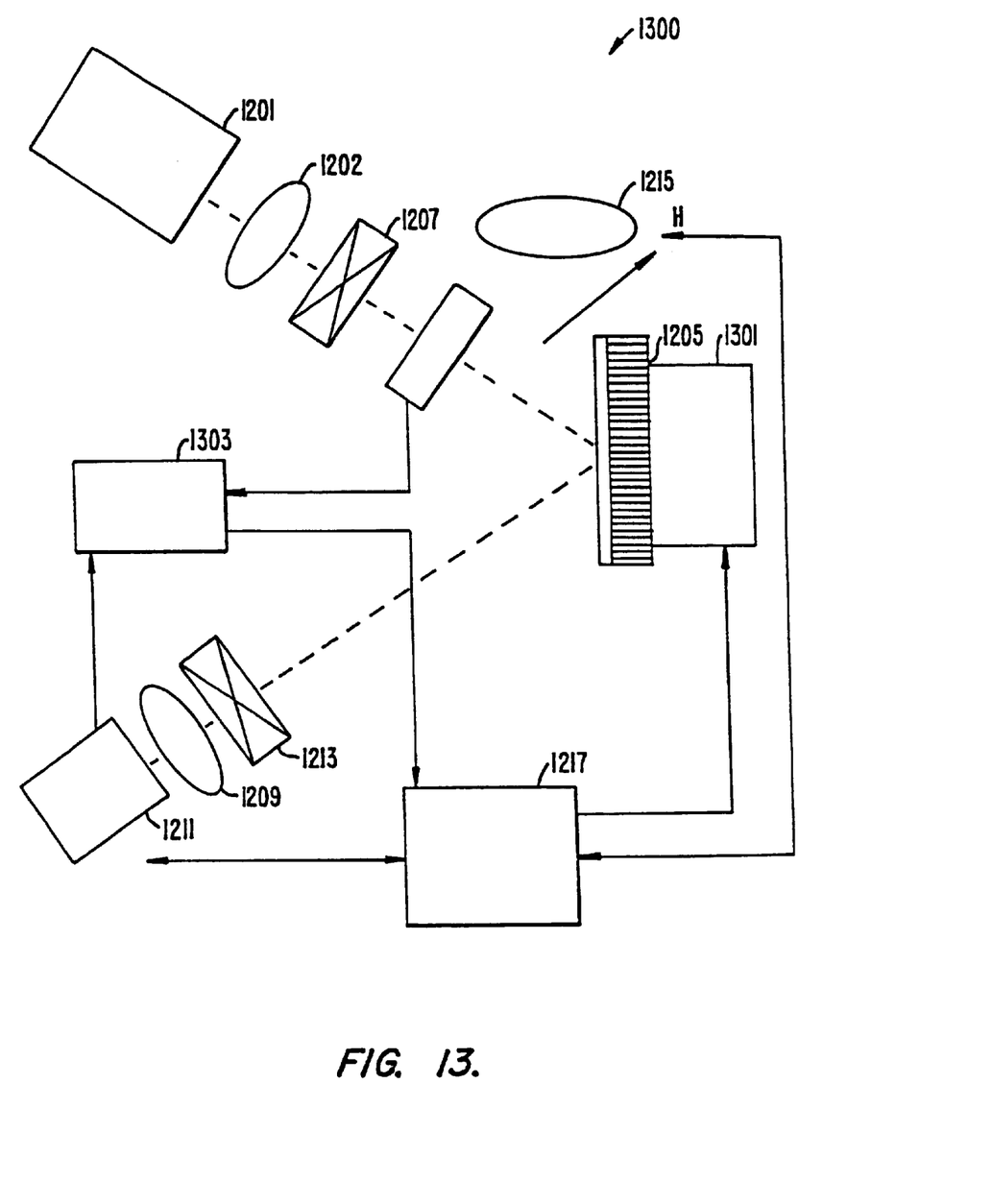
FIG. 13 illustrates an alternate configuration of the embodiment shown in FIG. 12 in which a translation stage scans the library in front of the source so that data is taken point-by-point.

FIG. 13 illustrates another embodiment of the optical system 1200 for measuring the Kerr rotation of different materials on a library 1205 of materials. As shown, system 1300 is similar to the previous embodiment, including a light source 1201, optical train 1203 and polarizer 1207 for directing polarized, filtered light onto library 1205, and a second polarizer 1213 and collection optics 1209 for imaging the reflected light onto light detector 1211. In this embodiment, light source 1201 is a point source and light detector 1211 is a single element detector (e.g., PMT or photodiode). The system includes a translation stage 1301 for scanning library 1205 in front of the beam so that the data is taken point-by-point. The advantage to this implementation is that the beam may be chopped and a lock-in detection system 1303 used to increase sensitivity.

Parallel Screening of Photon Emissions from Libraries

Figure 14:
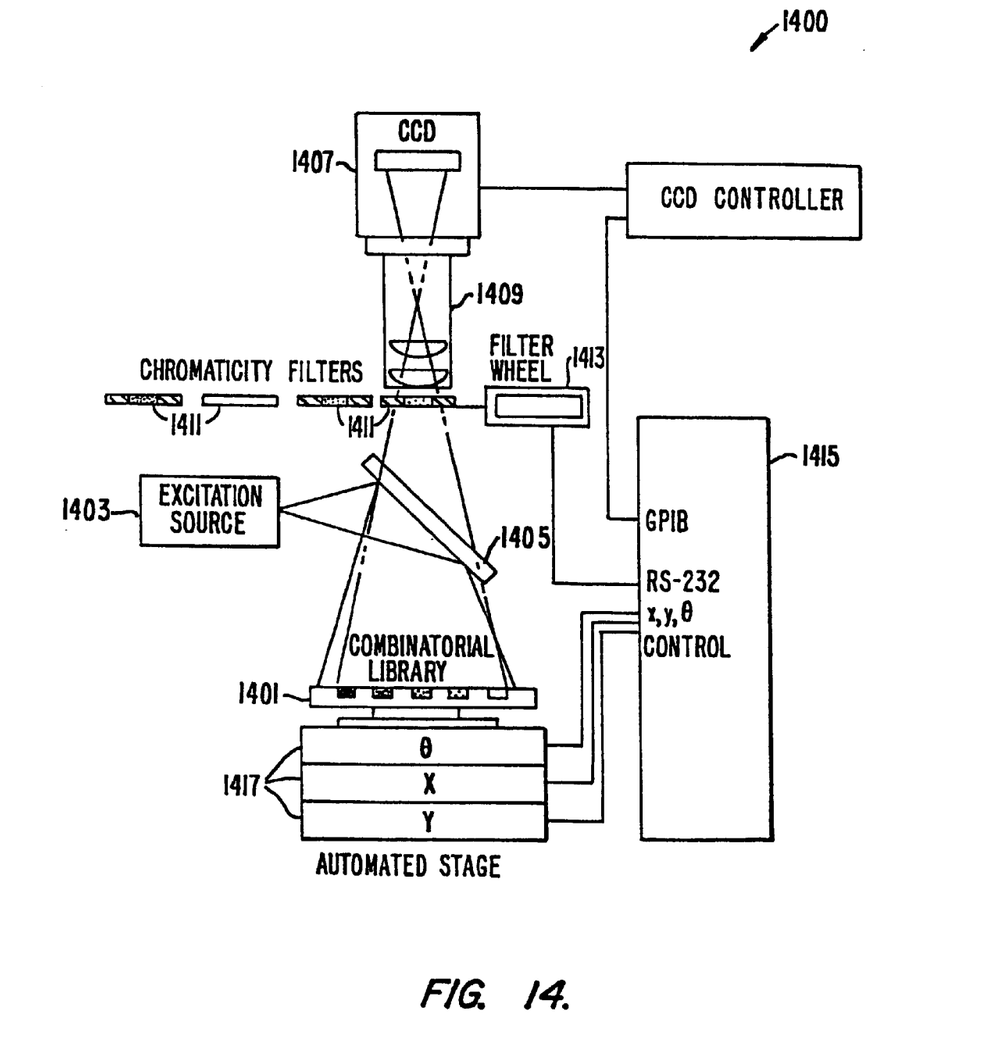
FIG. 14 illustrates an embodiment of the invention used to characterize the relative radiance, luminance, and chromaticity of an array of materials.

In another aspect of the invention illustrated in FIG. 14, a high throughput screening system 1400 is used to characterize the relative radiance, luminance, and chromaticity of samples with respect to spatial location within the array, excitation energy, and spectral output. Combinatorial libraries 1401 of luminescent materials or suitably tagged or coated samples are excited by a source 1403. Source 1403 is selected from a variety of sources including, but not limited to, VUV, visible/NIR, x-ray, and electron beam sources. In this embodiment the radiation from source 1403 is directed towards array 1401 with a beamsplitter 1405. The resulting photon emission passes through beamsplitter 1405 and is imaged onto an array detector 1407 by an optical train 1409. Array detector 1407 may be a CCD, CID, CMOS, or other array. The photon emission passes through a spectral filter 1411 prior to being detected by array 1407. Filters 1411 are held within a filter wheel 1413, preferably controlled by a processor 1415. Light emitting diodes (LEDs) and/or reference lumiphores (not shown), with known radiance, luminance, and chromaticty characteristics are used to calibrate the system and calculate the sample properties. The LEDs are housed in miniaturized (e.g., approximately ½ inch diameter) integrating spheres; for the reference lumiphores standard deep-powder plaques are employed. Translation stages 1417, preferably controlled by processor 1415, enable the rapid, segmented analysis of large-area samples in a fully automated manner.

In the preferred embodiment the entire system is automated and controlled by processor 1415. The sequence of steps for screening a luminescent library include; (i) detector and stage alignment, (ii) excitation field compensation, (iii) imaging of the reference standards, (iv) library alignment, and (v) library imaging/spectroscopy.

The step of aligning the array detector and the stage is required in order to determine a scaling factor between the pixels of the array and spatial positions within the library. Thus this step provides a mechanism for calculating distances between tiles and compensating for any possible misalignment of the stage with respect to the detector array. Due to the fact that the excitation field is generally not homogeneous, any nonuniformity of the field is characterized and compensated for with image processing algorithms performed in the frequency domain in all subsequent data analyses. Reference standards are employed to determine the radiance, luminance, and chromaticity of the library elements. Exposure conditions (e.g., integration time) for various excitation-observation conditions are determined based on observation of these reference standards with operation of the detector in a suitable regime (i.e., linear and unsaturated).

Subsequent to library acquisition, a linkage to the synthesis map is performed by means of a rotational alignment and single-point registration. Table 1 below is an example of a portion of a property table generated as a result of such an acquisition for a discrete library (row, column orientation).

TABLE 1

Property Table#

| Row | Column | CIE x | CIE y | Radiance $(W/m^2 sr)$ | Radiance Std. Dev. | Luminance $(cd/m^2)$ | Luminance Std. Dev. |
|---|---|---|---|---|---|---|---|
| Red LED ref. | | 7.18E−1 | 2.80E−1 | 3.1652E−2 | 2.3531E−3 | −2.9721E−1 | 1.4025E−1 |
| Green LED ref. | | 1.71E−1 | 6.89E−1 | 3.1884E−2 | 2.5880E−3 | 1.9115E+1 | 1.6621E+0 |
| Blue LED ref. | | 1.28E−1 | 8.72E−2 | 6.2998E−2 | 5.3813E−3 | 4.0730E+0 | 3.6883E−1 |
| White LED ref. | | 2.91E−1 | 3.06E−1 | 2.5318E−2 | 2.5856E−3 | 7.0099E+0 | 9.0734E−1 |
| $Y_2O_2S$:Eu 5% Powder | | 6.54E−1 | 3.45E−1 | 2.1902E−1 | 1.0389E−2 | 1.3732E+1 | 1.5324E+0 |
| 1 | 1 | 5.43E−1 | 2.32E−1 | 3.6204E−2 | 2.1836E−3 | 2.0328E+0 | 3.4037E−1 |
| 1 | 2 | 2.63E−1 | 1.98E−1 | 4.1475E−2 | 2.9413E−3 | 2.4121E+0 | 4.6172E−1 |
| ... | ... | ... | ... | ... | ... | ... | ... |
| ... | ... | ... | ... | ... | ... | ... | ... |
| 10 | 12 | 6.33E−1 | 2.75E−1 | 1.6326E−2 | 9.4503E−4 | 2.0515E+0 | 2.7395E−1 |

System 1400 can also be used to determine reflectance data for a combinatorial library, preferably at 0 degrees angle of incidence (i.e., 0/D). This determination does require changes in the post-processing software. Addition variables such as temperature may be employed during the library analyses.

In another embodiment, source 1403 is pulsed (i.e., modulated) and used in conjunction with a gated array detector to provide time-resolved luminescence information. By operating the array detector in a time-correlated manner with respect to the excitation source, dynamic data is acquired for the combinatorial library being investigated.

In another embodiment, automated stage 1417 is used to perform rapid, serial scanning across a combinatorial library. This strategy is adopted when either the excitation source is not amenable to large area illumination (e.g. focussed electron beam, IR probe, etc.) or high-resolution spectral analysis is required. Processor 1415 can be used in conjunction with stage 1417 to provide unattended analysis of large area combinatorial libraries in this manner.

In another embodiment utilizing a transparent substrate (not shown), system 1400 may be used to acquire spatially resolved absorption data for elements 1401 of the combinatorial library.

As will be understood by those familiar with the art, the present invention may be embodied in other specific forms without departing from the spirit or essential characteristics thereof Accordingly, disclosure of the preferred embodiment of the invention is intended to be illustrative, but not limiting, of the scope of the invention set forth in the following claims.

What is claimed is:

1. A method of characterizing members in an array of materials, comprising the steps of:
   providing a conducting substrates thereon a plurality of different materials in predefined regions and an optically active layer on said different materials, said optically active layer including an electroluminescent material, applying a voltage to said substrate;

monitoring intensity of luminescence of said array of materials as a function of applied voltage;

comparing members of said array with respect to said luminescence; and identifying materials for large scale preparation based upon said comparing step.

2. The method of claim 1 wherein said array has at least 9 different materials.

3. The method of claim 1 wherein said array has at least 50 different materials.

4. The method of claim 1 wherein said array has at least $10^3$ different materials.

5. The method of claim 1 wherein said array has at least $10^4$ different materials.

6. The method of claim 1 wherein said array has at least $10^5$ different materials.

7. The method of claim 1 wherein said array has at least $10^6$ different materials.

8. The method of claim 1 wherein said materials in said array have at least 3 components therein.

9. The method of claim 1 wherein said materials in said array have at least 4 components therein.

10. The method of claim 1 wherein said materials in said array have at least 5 components therein.

11. The method of claim 1 wherein said materials in said array have at least 6 components therein.

12. The method of claim 1 wherein said materials in said array have at least 7 components therein.

13. The method of claim 1 wherein said materials in said array have at least 8 components therein.

14. The method of claim 1 further comprising the step of providing data about each member of said array for ranking of said members with respect to dielectric coefficients based upon said luminescence.

15. The method of claim 1 wherein said different materials are provided on said substrate as deposited at a thickness of approximately 800 nm to 1200 nm.

16. The method of claim 1 wherein said voltage applying step is performed by increasing voltage.

17. The method of claim 1, wherein a transparent conducting overlayer is provided on said optically active layer.

18. The method of claim 17 wherein said voltage ranges up to about 20 volts.

19. The method of claim 1 wherein said electroluminescent material is ZnS:Mn.

20. The method of claim 1 wherein said predefined regions are contiguous with each other.

21. The method of claim 15 wherein said optically active layer has a thickness of about 100 to 500 nm.

22. The method of claim 1 wherein at least one member of said array is a standard dielectric material.

23. The method of claim 22 further comprising quantitatively comparing members of said array with said standard dielectric material.

* * * * *